United States Patent [19]

Buker et al.

[11] Plant 4,380

[45] Feb. 13, 1979

[54] **DISTINCT VARIETY OF KENTUCKY BLUEGRASS (*POA PRATENSIS*)**

[75] Inventors: Robert J. Buker, West Lafayette; Philip R. Troutman, Battleground, both of Ind.

[73] Assignee: FFR Cooperative, West Lafayette, Ind.

[21] Appl. No.: 910,140

[22] Filed: May 26, 1978

[51] Int. Cl.[2] ..... A01H 5/12

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—John R. Nesbitt

[57] ABSTRACT

A Kentucky bluegrass plant that is highly apomictic, thus providing a more uniform turf when propagated from seeds. The plant has good resistance to most diseases such as stripe smut, Helminthosporium leafspot, dollarspot, and rust. The production of a high number of rhizomes presents a dense turf which keeps weed competition down. This low-growing cultivar has a medium-textured turf and maintains its medium-green color for a longer season than some other varieties of bluegrass. The new variety of Kentucky bluegrass plant was selected from a large number of other bluegrass plants released in 1969 by Rutgers University to FFR Cooperative for variety development. The new variety was the result of replicated tests in cultivated areas at West Lafayette, Indiana and Spokane, Washington as reported hereinafter and the variety subsequently has been named "Plush". The variety is characterized by its ability to maintain a high turf quality over a wide geographical area and its ability to withstand, better than most bluegrasses, the high summertime temperatures. The qualities and charactristics which this new variety yields make it desirable in lawns and presents itself as an excellent seed producer.

1 Drawing Figure

BACKGROUND OF THE INVENTION

After this new Kentucky bluegrass plant was selected, it and 82 other selections were planted at West Lafayette, Ind. These selections were screened in replicated tests at West Lafayette, Ind., and Spokane, Wash., for seed yield, plant diseases, and/or general clonal performance. Promising material was seeded in 3-foot × 5-foot replicated turf plots in 1969. This new Kentucky bluegrass selection was labeled by FFR as 9031 and entered in several university tests as P-133. Subsequently, 9031 was named Plush by the Board of Directors of FFR Cooperative.

The new cultivar has been asexually reproduced by applicants by tiller division and the distinguishing characteristics remain true through succeeding generations.

DESCRIPTION OF THE DRAWINGS

FIG. 1 is a photograph showing the seedling of Plush variety bluegrass.

DETAILED DESCRIPTION OF THE NEW VARIETY

The new Plush variety of Kentucky bluegrass possesses the following combination of characteristics:

1. Highly apomictic.
2. Maintains good quality turf over a wide geographical area.
3. Excellent stripe smut (*Ustilago striiformis*) resistance.
4. Good Helminthosporium leafspot resistance.
5. Good dollarspot (*Sclerotinia homoeocarpa*) resistance.
6. Good rust (Puccinia spp.) tolerance.
7. Moderate Fusarium blight susceptibility.
8. Establishes faster than most other Kentucky bluegrasses.
9. Produces a dense turf.
10. Lower growing.

11. Medium-green color that develops early and lasts later.
12. Upright leaves with a medium width.
13. Medium thatch accumulation.
14. Establishes fast when sodded.
15. Good heat tolerance.
16. Excellent seed production characteristics.

The characteristics of the new variety described above are hereafter described in more detail, and it should be noted that comparisons made in all tests are to other bluegrasses grown and managed in a similar manner to Plush. Plush is not compared to all bluegrasses grown, but only to recently improved varieties. These comparisons are not by only one observation, but in replicated tests.

Highly apomictic: Plush is highly apomictic, in that progeny of the maternal plant will resemble the maternal parent. This provides a uniform-looking turf. (Table 1)

Maintains a good quality turf over a wide geographical area: Some Kentucky bluegrasses that were selected in a specific area do not adapt very well to other regions of Kentucky bluegrass growing area. This often leads to an inferior quality turf such as experienced with Nugget, an Alaskan selection, when grown in the Midwest and South. Plush, a Northeastern selection, has maintained a good quality turf over a wide geographical area. Plush has ranked high in turf quality in tests at Rutgers University, Virginia Polytechnic Institute and State University, University of Illinois, University of Missouri, and FFR Cooperative (Tables 2, 3, 4, 5, 6, and 7).

Excellent stripe smut (*Ustilago striiformis*) resistance: Stripe smut is a fungus that attacks the leaves and floral parts of Kentucky bluegrass. This drastically lowers the quality of turf or reduces seed yield in production fields. Plush has good resistance to stripe smut. (Table 8)

Good Helminthosporium leafspot resistance: In the past, Helminthosporium leafspot, characterized by dark, purplish-red lesions on the leaves, has severely limited the production of good quality turf. As the disease progresses, the "melting-out" phase begins. This results in large patches of dead plants appearing in the turf. Plush has good resistance to Helminthosporium leafspot. (Tables 9, 10, 11, and 12)

Good dollarspot (*Sclerotinia homoeocarpa*) resistance: Although dollarspot is not a major disease, its presence can form several blighted areas, about the size of a silver dollar, in the turf. In tests at the University of Illinois, Plush has shown to have good dollarspot resistance (Table 13).

Good rust (Puccinia spp.) tolerance: A disease that severely damages Merion Kentucky bluegrass is leaf rust. Plush has good tolerance to rust in tests at FFR Cooperative, while Merion is severely damaged (Table 14).

Moderate Fusarium blight susceptibility: Fusarium blight is becoming a major disease of Kentucky bluegrass turfs that are under high management. Plush is slightly susceptible to Fusarium blight, but has better tolerance and resistance than Fylking and Pennstar in tests at Rutgers (Table 15).

Establishes faster than most other Kentucky bluegrasses: Weed competition often ruins a turf when seedlings are emerging. Good seedling vigor is characterized by germinating and spreading fast, thus establishing a dense turf. In tests at FFR Cooperative, Plush had better seedling vigor than most other elite Kentucky bluegrasses (Table 16).

Produces a dense turf: A dense turf does not only look attractive, but also hinders weed growth. One grass weed that causes major problems in turf is annual bluegrass (*Poa annua*). At the University of Illinois, a trial to measure the competitive ability of Kentucky bluegrass in annual bluegrasses was conducted. Ten-centimeters-in-diameter plugs of Kentucky bluegrass varieties from a two-year-old turf plot were placed in a solid stand of *Poa annua*. The trial was managed under conditions favorable to the development of annual bluegrass. After fourteen months, the plugs were measured to determine how much the *Poa annua* took over the plug. Because of its capability to produce a dense turf, Plush still had a diameter of 7.9 centimeters while several other bluegrass varieties had measurements of less than 7.0 centimeters (Table 17).

Kentucky bluegrass spreads by rhizomes. The more rhizomes per square foot, the better the density of the turf. In tests at Virginia Polytechnic Institute and State University, Plush had good rhizome production (Table 18).

In turf trials at FFR Cooperative, ratings for density were taken 12 and 30 months after seeding. Plush had a better density than Sodco at 12 months, and better than several other varieties at 30 months (Table 19).

Lower growing: Plush has a semi-dwarf growth characteristic. The plant height of Plush in an uncut turf situation is shorter than Fylking or Merion (Table 20).

Medium-green color that develops early and lasts late: Plush has lighter-green color than Adelphi, but is darker than Park. (Tables 21 and 22) This medium-green color tends to make many of the turf weeds, which tend to be lighter green, less noticeable when present. Plush's color develops early in the spring, earlier than Nugget or Cougar (Table 23). Plush maintains its medium-green color longer into the fall and early winter than Merion, Kenblue, or Park (Table 24).

Upright leaves with a medium width: Plush's leaves tend to be more upright. This makes leaves easier to cut. Plush's leaf angle from the central axis is approximately 36°, compared to 51° for Merion (Table 25). The leaves of Plush are medium width. They are wider than Nugget and Fylking, but narrower than Merion (Table 25).

Medium thatch accumulation: Thatch is a major problem for newer turfgrasses. The build-up of non-decmposed, dead vegetative matter becomes a favorable environment for diseases. Plush has a thatch depth of 1.33 centimeters, compared to Nugget's 1.52 centimeters, in tests at the University of Illinois (Table 26).

Establishes fast when sodded: The ability of a Kentucky bluegrass to recover and start growing is very important when laying sod. One way to measure this ability is the root strength test. In this test, a one-foot-square piece of turf is pulled from the soil surface after it has had time to establish its roots. The pounds of force required to pull this from the surface give a good indication of how fast the variety recovers after being sodded. Plush had an average root pull strength of 335 pounds in tests at Virginia Polytechnic Institute and State University, compared to Merion's 266 pounds (Table 27).

Good heat tolerance: One aspect that limits the growth of Kentucky bluegrass in southern regions of bluegrass belt is its tolerance to the hot summertime temperatures. At Virginia Polytechnic Institute and State University, several Kentucky bluegrass cultivars were placed in a growth chamber. These six-inch-square pieces of sod were exposed to temperatures 50° C. for 16 hours and 30° C. for 8 hours for each day over a seven-day period. After the treatment, they were removed from chamber and sodded. Plush had retained 53% of its greenness, compared to Adelphi's 30%, Merion's 33%, or Kenblue's 65% (Table 28). After the cultivars were sodded, their recovery rates were measured by their root strength for a 6-inch-square piece of sod and percent ground cover. Plush had ratings of 85 pounds and 72 percent spread, respectively, compared to Adelphi's 58 pounds and 58% ground cover (Table 28).

Excellent seed production characteristics: In order to have a successful variety, seed must be plentiful and at a reasonable cost. A Kentucky bluegrass cultivar must have a good seed yield to be successful. Several factors determine a good yield. It must have good lodging resistance to prevent the seed head from lying on the ground. In tests at Spokane, Washington, Plush has good lodging resistance (Table 29). In order to harvest the seed more easily, the inflorescence should be high above vegetative material. Plush produces a culm of about 72 centimeters. Plush has a seed head higher than Nugget (Table 30). Also, the cultivar should be early-maturing. Early-maturing varieties in dry land production can take advantage of the winter moisture. Plush is earlier-maturing than Merion or Sodco (Table 31). Plush's seed yield is comparable to that of Fylking and Merion in tests at Spokane, Washington (Table 32).

The seed of Plush is darker in color than Merion or Baron, but is lighter than Adelphi or Nugget (Table 33). Plush has a larger seed size than most Kentucky bluegrasses (Table 33). Larger seeds usually have better germination vigor than small seeds.

TABLE 1

| Seed Source | Percent Apomixis in Plush[a] Number of Plants Tested | % Maternal-like Plants |
|---|---|---|
| Lot SW71 | 200 | 86 |
| Lot RU69 | 350 | 89 |
| Lot RU73 | 100 | 87 |
| Total | 650 | Mean 87.33 |

[a]1974 Apomixis Test of Plush Kentucky Bluegrass at FFR Cooperative, West Lafayette, Indiana.
P. R. Troutman

TABLE 2

Turf Quality at Rutgers University[a]

| Variety | 1972 | 1973 | 1974 | 1975 | 4-year mean |
|---|---|---|---|---|---|
| Rating: 9 = best; 1 = poor | | | | | |
| Plush | 6.0 | 6.5 | 6.7 | 6.5 | 6.4 |
| Adelphi | 7.0 | 6.7 | 6.8 | 6.9 | 6.8 |
| Baron | 4.5 | 5.7 | 5.8 | 5.1 | 5.3 |
| Bonnieblue | 6.3 | 6.7 | 6.8 | 6.6 | 6.6 |
| Brunswick | 5.5 | 6.9 | 7.5 | 7.3 | 6.8 |
| Fylking | 6.0 | 6.3 | 5.7 | 4.5 | 5.6 |
| Galaxy | 6.3 | 6.4 | 6.1 | 5.6 | 6.1 |
| Glade | 6.5 | 6.5 | 6.7 | 6.7 | 6.6 |
| Kenblue | 4.0 | 3.0 | 3.3 | 2.8 | 3.3 |
| Majestic | 7.3 | 7.0 | 6.3 | 6.0 | 6.6 |
| Merion | 6.3 | 6.8 | 6.6 | 5.7 | 6.4 |
| Monopoly | 4.5 | 5.5 | 5.4 | 6.3 | 5.4 |
| Nugget | 7.0 | 5.3 | 5.0 | 4.2 | 5.4 |
| Park | 3.8 | 2.9 | 3.0 | 2.1 | 3.0 |
| Pennstar | 6.0 | 6.5 | 5.7 | 4.6 | 5.7 |
| Sodco | 6.8 | 6.7 | 6.8 | 6.3 | 6.6 |
| Sydsport | 5.0 | 6.0 | 6.4 | 6.3 | 5.9 |
| Vantage | 3.3 | 5.1 | 5.7 | 5.5 | 5.0 |
| Victa | 4.5 | 5.7 | 5.8 | 5.4 | 5.4 |
| Windsor | 4.5 | 5.5 | 6.4 | 7.1 | 5.9 |
| Grand Mean | | | | | 5.7 |

[a]1972 Regional Test of Kentucky Bluegrass and Fine Fescue varieties at Rutgers University.
C. Reed Funk

TABLE 3

Turf Quality at Virginia Polytechnic Institute and State University[a]

| Variety | 1973 | 1974 | 1975 | 3-year mean |
|---|---|---|---|---|
| Rating: 9 = best; 1 = poor | | | | |
| Plush | 7.5 | 7.2 | 5.2 | 6.6 |
| Adelphi | 7.4 | 7.2 | 5.4 | 6.8 |
| Baron | 6.7 | 6.5 | 5.1 | 6.1 |
| Bonnieblue | 7.7 | 6.9 | 5.3 | 6.6 |
| Brunswick | 7.8 | 6.7 | 5.1 | 6.5 |
| Fylking | 6.6 | 6.1 | 4.5 | 5.7 |
| Galaxy | 7.6 | 6.7 | 4.7 | 6.3 |
| Glade | 7.1 | 6.5 | 5.4 | 6.3 |
| Kenblue | 7.0 | 5.9 | 5.1 | 6.0 |
| Majestic | 7.4 | 7.1 | 5.3 | 6.6 |
| Merion | 6.8 | 6.1 | 5.4 | 6.1 |
| Monopoly | 7.4 | 7.1 | 5.7 | 6.8 |
| Nugget | 6.2 | 6.1 | 5.0 | 5.8 |
| Park | 6.2 | 5.6 | 4.6 | 5.4 |
| Pennstar | 7.5 | 6.4 | 4.7 | 6.2 |
| Sodco | 7.9 | 6.9 | 5.8 | 6.9 |
| Sydsport | 7.4 | 6.9 | 5.4 | 6.6 |
| Vantage | 7.1 | 6.0 | 5.3 | 6.1 |
| Victa | 6.9 | 6.9 | 5.6 | 6.5 |
| Windsor | 7.3 | 6.4 | 4.6 | 6.1 |
| Grand Mean | | | | 6.3 |

[a]1972 Regional Kentucky Bluegrass Test at Virginia Polytechnic Institute and State University.
Lincoln Taylor.

TABLE 4

Turf Quality at University of Illinois[a]

| Variety | 1973 Mean | 1974 Mean | 1975 Mean | 3-Year Mean |
|---|---|---|---|---|
| Rating: 1 = best; 9 = poor | | | | |
| Plush | 2.9 | 2.6 | 2.3 | 2.6 |
| Adelphi | 2.6 | 2.4 | 3.2 | 2.7 |
| Baron | 2.9 | 3.2 | 3.4 | 3.2 |
| Bonnieblue | 3.1 | 3.1 | 3.0 | 3.1 |
| Brunswick | 2.6 | 2.8 | 3.0 | 2.8 |
| Fylking | 2.9 | 3.3 | 3.3 | 3.2 |

TABLE 4-continued

Turf Quality at University of Illinois[a]

| Variety | 1973 Mean | 1974 Mean | 1975 Mean | 3-Year Mean |
|---|---|---|---|---|
| Galaxy | 3.0 | 2.8 | 3.0 | 2.9 |
| Glade | 2.8 | 2.7 | 3.5 | 3.0 |
| Kenblue | 4.6 | 3.8 | 3.5 | 4.0 |
| Majestic | 3.0 | 2.7 | 3.2 | 3.0 |
| Merion | 3.2 | 2.9 | 2.6 | 2.9 |
| Monopoly | 3.1 | 2.1 | 2.2 | 2.5 |
| Nugget | 3.1 | 3.6 | 5.0 | 3.9 |
| Park | 4.9 | 3.3 | 3.0 | 3.7 |
| Pennstar | 3.1 | 3.5 | 3.3 | 3.3 |
| Sodco | 3.0 | 2.9 | 2.8 | 2.9 |
| Sydsport | 2.7 | 2.7 | 4.0 | 3.1 |
| Vantage | 3.3 | 2.9 | 2.7 | 3.0 |
| Victa | 3.0 | 3.1 | 3.0 | 3.0 |
| Windsor | 3.0 | 2.5 | 2.4 | 2.6 |
| Grand Mean | | | | 3.1 |

[a]1972 Regional Bluegrass Trials at University of Illinois.
A. J. Turgeon

TABLE 5

Turf Quality at the Southwest Research Center of the University of Missouri[a]

| Variety | 3-Year Mean |
|---|---|
| Rating: 9 = best; 1 = poor | |
| Plush | 4.6 |
| Adelphi | 4.5 |
| Baron | 4.6 |
| Bonnieblue | 4.6 |
| Brunswick | 4.8 |
| Fylking | 4.3 |
| Galaxy | 4.7 |
| Glade | 4.3 |
| Kenblue | 3.4 |
| Majestic | 4.5 |
| Merion | 3.3 |
| Monopoly | 4.6 |
| Nugget | 3.0 |
| Park | 4.1 |
| Pennstar | 4.1 |
| Sodco | 4.1 |
| Sydsport | 4.5 |
| Vantage | 4.1 |
| Victa | 4.9 |
| Windsor | 4.3 |
| Grand Mean | 4.3 |
| LSD at 5% Level | .5 |

[a]1972 Regional Test of Kentucky Bluegrass at the Southwest Research Center of the University of Missouri.
John H. Dunn

TABLE 6

Turf Quality at FFR Cooperative[a]

| Variety | 1970 | 1971 | 1973 | 3-year Mean |
|---|---|---|---|---|
| Rating: 1 = best; 9 = poor | | | | |
| Plush | 3.9 | 3.4 | 2.8 | 3.4 |
| Cougar | 3.5 | 5.4 | 4.4 | 4.4 |
| Delta | 6.1 | 7.3 | 6.1 | 6.5 |
| Fylking | 3.9 | 4.7 | 4.1 | 4.2 |
| Geary | 5.9 | 6.6 | 5.2 | 5.9 |
| Kenblue | 5.3 | 7.2 | 6.3 | 6.3 |
| Merion | 3.3 | 3.8 | 4.3 | 3.8 |
| Newport | 4.7 | 5.8 | 6.0 | 5.5 |
| Nudwarf | 5.9 | 6.1 | 6.5 | 6.2 |
| Nugget | 4.0 | 4.3 | 3.5 | 3.9 |
| Park | 6.3 | 6.0 | 5.7 | 6.0 |
| Sodco | 5.8 | 6.4 | 6.5 | 6.2 |
| S-21 | 6.5 | 6.3 | 6.6 | 6.5 |
| S. Dakota Common | 5.8 | 6.4 | 6.5 | 6.2 |
| Grand Mean | | | | 5.4 |
| LSD at 5% Level | 1.38 | 1.17 | 1.44 | |

[a]Turf Evaluations at FFR Cooperative, West Lafayette, Indiana.
P. R. Troutman

TABLE 7

Turf Quality Averaged Across Five Locations

| Variety | Rutgers | VPI | Location Missouri | Ill | FFR | Mean |
|---|---|---|---|---|---|---|
| Rating[b]: 9 = best; 1 = poor | | | | | | |
| Plush | 6.4 | 6.6 | 4.6 | 7.4 | 6.7 | 6.3 |

TABLE 7-continued

| Variety | Turf Quality Averaged Across Five Locations | | | | | |
|---|---|---|---|---|---|---|
| | Rutgers | VPI | Location Missouri | Ill | FFR | Mean |
| Adelphi | 6.8 | 6.8 | 4.5 | 7.3 | X[a] | X |
| Baron | 5.3 | 6.1 | 4.6 | 6.8 | X | X |
| Bonnieblue | 6.6 | 6.6 | 4.6 | 6.9 | X | X |
| Brunswick | 6.8 | 6.5 | 4.8 | 7.2 | X | X |
| Fylking | 5.6 | 5.7 | 4.3 | 6.8 | 5.8 | 5.6 |
| Galaxy | 6.1 | 6.3 | 4.7 | 7.1 | X | X |
| Glade | 6.6 | 6.3 | 4.3 | 7.0 | X | X |
| Kenblue | 3.3 | 6.0 | 3.4 | 6.0 | 3.8 | 4.5 |
| Majestic | 6.6 | 6.6 | 4.5 | 7.0 | X | X |
| Merion | 6.4 | 6.1 | 3.3 | 7.1 | 6.2 | 5.8 |
| Monopoly | 5.4 | 6.8 | 4.6 | 7.5 | X | X |
| Nugget | 5.4 | 5.8 | 3.0 | 6.1 | 6.1 | 5.3 |
| Park | 3.0 | 5.4 | 4.1 | 6.3 | 4.0 | 4.6 |
| Pennstar | 5.7 | 6.2 | 4.1 | 6.7 | X | X |
| Sodco | 6.6 | 6.9 | 3.9 | 7.1 | 3.8 | 5.7 |
| Sydsport | 5.9 | 6.6 | 4.5 | 6.9 | X | X |
| Vantage | 5.0 | 6.1 | 4.1 | 7.0 | X | X |
| Victa | 5.4 | 6.5 | 4.9 | 7.0 | X | X |
| Windsor | 5.9 | 6.1 | 4.3 | 6.4 | X | X |

[a]Not Tested in this Trial
[b]Rating for Illinois and FFR are converted to 9 = best; 1 = poor.

TABLE 8

| Variety | Stripe Smut Resistance at Rutgers University[a] Infected Tillers |
|---|---|
| | Number of tillers per square foot infected with stripe smut |
| Plush | 2 |
| Adelphi | 1 |
| Baron | 25 |
| Glade | 2 |
| Merion | 138 |
| Windsor | 90 |

[a]1972 Regional Kentucky Bluegrass Trials at Rutgers University.
C. Reed Funk

TABLE 9

| Variety | Helminthosporium Leafspot Tolerance at University of Illinois[a] | | | |
|---|---|---|---|---|
| | 1973 | 1974 | 1975 | 3-year mean |
| | Rating: 1 = best; 9 = poor | | | |
| Plush | 2.7 | 2.3 | 3.0 | 2.7 |
| Adelphi | 2.3 | 2.3 | 2.0 | 2.2 |
| Baron | 3.3 | 2.3 | 2.7 | 2.8 |
| Bonnieblue | 2.0 | 1.7 | 2.3 | 2.0 |
| Brunswick | 1.7 | 2.3 | 3.0 | 2.3 |
| Fylking | 2.7 | 2.0 | 2.3 | 2.3 |
| Galaxy | 1.7 | 1.3 | 2.0 | 1.7 |
| Glade | 3.0 | 2.3 | 2.7 | 2.7 |
| Kenblue | 5.7 | 5.7 | 5.0 | 5.5 |
| Majestic | 1.0 | 1.7 | 2.0 | 1.6 |
| Merion | 1.7 | 1.3 | 3.0 | 2.0 |
| Monopoly | 2.7 | 2.0 | 2.7 | 2.5 |
| Nugget | 2.0 | 1.3 | 1.0 | 1.4 |
| Park | 6.0 | 3.3 | 5.3 | 4.9 |
| Pennstar | 2.0 | 1.7 | 2.0 | 1.9 |
| Sodco | 3.0 | 2.7 | 3.0 | 2.9 |
| Sydsport | 2.0 | 2.3 | 2.0 | 2.1 |
| Vantage | 5.0 | 4.3 | 3.7 | 4.3 |
| Victa | 2.7 | 2.0 | 2.7 | 2.5 |
| Windsor | 3.0 | 2.7 | 3.0 | 2.9 |
| Mean | | | | 2.7 |

[a]1972 Regional Bluegrass Trials at University of Illinois
A. J. Turgeon

TABLE 10

| Variety | Helminthosporium Leafspot Tolerance at Virginia Polytechnic Institute and State University[a] 1974 Mean |
|---|---|
| | Rating: 9 = best; 1 = poor |
| Plush | 6.3 |
| Adelphi | 6.7 |
| Baron | 6.7 |
| Bonnieblue | 8.7 |
| Brunswick | 6.7 |
| Fylking | 6.7 |
| Galaxy | 7.3 |
| Glade | 4.3 |

TABLE 10-continued

| Variety | Helminthosporium Leafspot Tolerance at Virginia Polytechnic Institute and State University[a] 1974 Mean |
|---|---|
| Kenblue | 4.0 |
| Majestic | 7.7 |
| Merion | 7.0 |
| Monopoly | 6.0 |
| Nugget | 4.0 |
| Park | 7.0 |
| Pennstar | 6.7 |
| Sodco | 6.7 |
| Sydsport | 6.7 |
| Vantage | 7.0 |
| Victa | 6.7 |
| Windsor | 7.0 |
| Grand Mean | 6.5 |

[a]1972 Regional Bluegrass Trials at Virginia Polytechnic Institute and State University.
Lincoln Taylor

TABLE 11

| Entry | Helminthosporium Leafspot Tolerance at FFR Cooperative[a] | | | |
|---|---|---|---|---|
| | 5-5-72 | 4-19-73 | 5-22-74 | 3-year mean |
| | Rating[b]: 1 = best; 9 = poor | | | |
| Plush | 5.3 | 3.0 | 3.0 | 3.8 |
| Cougar | 6.3 | 4.3 | 5.0 | 5.2 |
| Delta | 5.0 | 8.3 | 6.7 | 6.7 |
| Fylking | 2.8 | 4.5 | 3.0 | 3.4 |
| Geary | 8.0 | 8.0 | 8.0 | 8.0 |
| Kenblue | 7.3 | 9.0 | 6.3 | 7.5 |
| Merion | 2.3 | 2.7 | 1.7 | 2.2 |
| Newport | 6.0 | 7.0 | 8.3 | 7.1 |
| Nudwarf | 7.3 | 9.0 | 7.3 | 7.9 |
| Nugget | 2.6 | 2.5 | 1.4 | 2.2 |
| Park | 7.0 | 9.2 | 6.7 | 7.6 |
| Sodco | 3.0 | 3.2 | 2.8 | 3.0 |
| S-21 | 7.0 | 8.3 | 7.0 | 7.4 |
| S. Dakota Common | 8.0 | 8.7 | 7.3 | 8.0 |
| Grand Mean | | | | 5.7 |
| LSD at 5% Level | 1.8 | 2.1 | 1.5 | |

[a]Turf Evaluations at FFR Cooperative, West Lafayette, Indiana
P. R. Troutman
[b]Rating for Helminthosporium tolerance:
1 = good tolerance
9 = poor tolerance

TABLE 12

| Variety | Helminthosporium Leafspot Tolerance Summary of the Three Locations | | | |
|---|---|---|---|---|
| | U. of Illinois[a] | VPI & SU[b] | FFR | Mean |
| | Ratings: 1 = best; 9 = poor | | | |
| Plush | 2.7 | 3.7 | 3.8 | 3.4 |
| Adelphi | 2.2 | 3.3 | X[c] | X |
| Baron | 2.8 | 3.3 | X | X |
| Bonnieblue | 2.0 | 1.3 | X | X |
| Brunswick | 2.3 | 3.3 | X | X |
| Fylking | 2.3 | 3.3 | 3.4 | 3.0 |
| Galaxy | 1.7 | 2.7 | X | X |
| Glade | 2.7 | 5.7 | X | X |
| Kenblue | 5.5 | 6.0 | 7.5 | 6.3 |
| Majestic | 1.6 | 2.3 | X | X |
| Merion | 2.0 | 3.0 | 2.2 | 2.4 |
| Monopoly | 2.5 | 4.0 | X | X |
| Nugget | 1.4 | 6.0 | 2.2 | 3.2 |
| Park | 4.9 | 3.0 | 7.6 | 5.2 |
| Pennstar | 1.9 | 3.3 | X | X |
| Sodco | 2.9 | 3.3 | 3.0 | 3.1 |
| Sydsport | 2.1 | 3.3 | X | X |
| Vantage | 4.3 | 3.0 | X | X |
| Victa | 2.5 | 3.3 | X | X |
| Windsor | 2.9 | 3.0 | X | X |
| Grand Mean | | | | 3.1 |

[a]Summary of the three tables (9a, 9b, and 9c).
[b]The ratings for Virginia Polytechnic Institute and State University are converted to a 1 = best, 9 = poor scale (table 9b).
[c]Not in this test

TABLE 13

Dollarspot Resistance at the University of Illinois[a]

| Variety | 1975 |
|---|---|
| Rating: 1 = most resistance; 9 = least | |
| Plush | 1.0 |
| Adelphi | 1.0 |
| Baron | 1.0 |
| Bonnieblue | 1.0 |
| Brunswick | 1.7 |
| Fylking | 1.3 |
| Galaxy | 1.0 |
| Glade | 1.7 |
| Kenblue | 1.3 |
| Majestic | 1.0 |
| Merion | 1.3 |
| Monopoly | 1.0 |
| Nugget | 3.3 |
| Park | 1.0 |
| Pennstar | 1.0 |
| Sodco | 1.0 |
| Sydsport | 1.0 |
| Vantage | 1.0 |
| Victa | 1.0 |
| Windsor | 1.0 |

[a]1972 Regional Kentucky Bluegrass Trials at the University of Illinois.
A. J. Turgeon

TABLE 14

Rust Tolerance at FFR Cooperative[a]

| Variety | 1970 | 1973 | 2-year Mean |
|---|---|---|---|
| Rating: 1 = best; 9 = poor | | | |
| Plush | 1.3 | 1.7 | 1.5 |
| Cougar | 1.7 | 2.3 | 2.0 |
| Delta | 2.3 | 1.0 | 1.6 |
| Fylking | 1.2 | 2.7 | 2.0 |
| Geary | 1.7 | 2.3 | 2.0 |
| Kenblue | 1.0 | 3.7 | 2.4 |
| Merion | 7.0 | 9.0 | 8.0 |
| Newport | 1.7 | 1.7 | 1.7 |
| Nudwarf | 1.3 | 2.7 | 2.0 |
| Nugget | 1.0 | 1.0 | 1.0 |
| Park | 1.7 | 4.0 | 2.8 |
| Sodco | 1.2 | 1.3 | 1.2 |
| S-21 | 2.0 | 2.7 | 1.4 |
| S. Dakota Common | 1.3 | 1.7 | 2.0 |
| Mean | | | 2.3 |
| LSD at 5% Level | 1.2 | 2.1 | |

[a]Kentucky Bluegrass Evaluations at FFR Cooperative.
P. R. Troutman

TABLE 15

Fusarium Blight Resistance at Rutgers University[a]

| Variety | Percent Damage 1974 | 1975 | Mean |
|---|---|---|---|
| Plush | 10.0 | 24.4 | 17.2 |
| Adelphi | 1.7 | .4 | 1.0 |
| Baron | 8.7 | 18.4 | 13.6 |
| Bonnieblue | 6.0 | 4.3 | 5.2 |
| Brunswick | 6.3 | 28.0 | 17.2 |
| Fylking | 17.0 | 30.8 | 23.9 |
| Galaxy | 7.7 | 8.4 | 8.0 |
| Glade | .7 | 7.0 | 3.8 |
| Kenblue | 3.3 | 6.3 | 4.8 |
| Majestic | 6.0 | 8.4 | 7.2 |
| Merion | 9.0 | 15.4 | 12.2 |
| Monopoly | 2.7 | .8 | 1.8 |
| Nugget | 5.3 | 29.2 | 17.2 |
| Park | 3.0 | 15.9 | 9.4 |
| Pennstar | 16.3 | 30.9 | 23.6 |
| Sodco | 4.7 | 5.3 | 5.0 |
| Sydsport | 1.7 | 3.0 | 2.4 |
| Vantage | 2.3 | 6.7 | 4.5 |
| Victa | 6.0 | 18.4 | 12.2 |
| Windsor | .7 | .3 | .5 |
| LSD at 5% Level | 5.7 | | |

[a]1972 Regional Kentucky Bluegrass Trials at Rutgers University.
C. Reed Funk

TABLE 16

Seedling Vigor at FFR Cooperative[a]

| Variety | Days after seeding 13 days | 33 days | 61 days | 71 days | Mean |
|---|---|---|---|---|---|
| Rating: 1 = most vigor; 9 = least | | | | | |
| Plush | 3.0 | 2.0 | 2.0 | 1.3 | 2.1 |
| Adelphi | 7.3 | 6.3 | 3.7 | 2.0 | 4.8 |
| Baron | 6.3 | 5.7 | 4.7 | 3.3 | 5.0 |
| Bonnieblue | 5.0 | 5.0 | 3.3 | 2.3 | 3.9 |
| Brunswick | 2.7 | 3.0 | 3.3 | 2.7 | 2.9 |
| Fylking | 4.7 | 4.0 | 2.3 | 2.3 | 3.3 |
| Glade | 3.0 | 3.3 | 3.3 | 1.7 | 2.8 |
| Kenblue | 3.0 | 2.0 | 2.0 | 1.7 | 2.2 |
| Majestic | 4.0 | 2.7 | 2.0 | 1.7 | 2.6 |
| Merion | 6.7 | 5.7 | 4.0 | 1.3 | 4.4 |
| Nugget | 4.7 | 3.0 | 4.7 | 2.7 | 3.8 |
| Park | 1.3 | 1.3 | 1.7 | 2.0 | 1.6 |
| Pennstar | 5.0 | 3.0 | 3.0 | 2.3 | 3.3 |
| Sodco | 6.3 | 4.7 | 3.7 | 2.3 | 4.3 |
| Sydsport | 6.7 | 6.0 | 4.3 | 3.3 | 5.1 |
| Vantage | 7.0 | 5.7 | 3.7 | 3.3 | 4.9 |
| Victa | 5.0 | 2.3 | 2.7 | 2.3 | 3.1 |
| Windsor | 5.0 | 4.0 | 3.0 | 2.0 | 3.5 |
| LSD at 5% Level | 2.10 | 1.51 | 1.72 | 0.71 | |

[a]1976 Kentucky Bluegrass Evaluations at FFR Cooperative.
P. R. Troutman

TABLE 17

Competitive ability of Kentucky Bluegrass Varieties in 0.75 in. Annual Bluegrass Turf at 14 Months[a]

| Plug Diameter (cm.) | Cultivar |
|---|---|
| 8.9 – 8.0 | Warren's A-20 Touchdown, Parade Glade, Baron, Brunswick |
| 7.9 – 7.0 | Plush, Kenblue Warren's A-34 Adelphi, Sydsport |
| 6.9 – 6.0 | Geronimo, Sodco Windsor, Nugget |
| 5.9 – 5.0 | Pennstar Victa Bonnieblue |
| 4.9 – 4.0 | Merion, Vantage Fylking |
| 3.9 – 3.0 | Majestic, Campina Monopoly |
| 2.9 – 2.0 | Park Galaxy |

[a]1972 Regional Kentucky Bluegrass Trials at University of Illinois.
A. J. Turgeon

TABLE 18

Rhizome Production of Kentucky Bluegrass Cultivars in July, 1974 at Virginia Polytechnic Institute and State University[a]

| Variety | Number of Rhizomes per Square Foot |
|---|---|
| Plush | 17 |
| Adelphi | 14 |
| Baron | 18 |
| Bonnieblue | 13 |
| Brunswick | 12 |
| Fylking | 9 |
| Galaxy | 19 |
| Glade | 13 |
| Kenblue | 8 |
| Majestic | 18 |
| Merion | 17 |
| Monopoly | 19 |
| Nugget | 11 |
| Park | 19 |
| Pennstar | 12 |
| Sodco | 14 |
| Sydsport | 15 |
| Vantage | 11 |
| Victa | 11 |
| Windsor | 12 |

[a]1972 Regional Kentucky Bluegrass Trials at Virginia Polytechnic Institute and State University.
R. E. Schmidt

TABLE 19

Turf Density at FFR Cooperative[a]

| Variety | 12 months | 30 months |
|---|---|---|
| Rating:[b] 1 = most dense; 9 = least dense | | |
| Plush | 5.4 | 2.5 |
| Belturf | 4.8 | 4.5 |
| Cougar | 4.8 | 3.5 |
| Delta | 4.2 | 6.5 |
| Fylking | 4.5 | 3.2 |
| Geary | 3.8 | 4.8 |

TABLE 19-continued

| Variety | Turf Density at FFR Cooperative[a] 12 months | 30 months |
|---|---|---|
| Kenblue | 4.0 | 7.8 |
| Merion | 5.5 | 4.8 |
| Newport | 4.0 | 5.0 |
| Nudwarf | 3.2 | 5.0 |
| Nugget | 5.4 | 7.2 |
| Park | 3.8 | 5.2 |
| Pennstar | 5.8 | 4.2 |
| Sodco | 7.2 | 6.5 |
| S-21 | 3.5 | 7.8 |
| S. Dakota Common | 3.4 | 6.8 |
| Windsor | 4.5 | 5.5 |
| LSD at 5% level | 1.3 | 2.4 |

[a]Turf Evaluations at FFR Cooperative.
P. R. Troutman
[b]Ratings taken 12 months and 30 months after seeding.

TABLE 20

| Variety | Turf Dwarfness at FFR Cooperative[a] Dwarfness[b] |
|---|---|
| Rating: 1 = 10 cm; 9 = 30 cm | |
| Plush | 2.9 |
| Cougar | 4.5 |
| Delta | 7.3 |
| Fylking | 6.8 |
| Geary | 5.9 |
| Kenblue | 7.3 |
| Merion | 3.5 |
| Newport | 5.1 |
| Nudwarf | 6.2 |
| Nugget | 2.2 |
| Park | 6.5 |
| Sodco | 3.9 |
| S-21 | 5.5 |
| S. Dakota Common | 6.5 |
| Mean | 5.3 |
| LSD at 5% Level | .7 |

[a]Bluegrass Evaluations at FFR Cooperative.
P. R. Troutman
[b]Rating is a mean of 12 observations from 1969–1974.

TABLE 21

| Variety | Turf Color at FFR Cooperative[a] 1976 |
|---|---|
| Rating: 1 = dark green; 9 = light green | |
| Plush | 4.7 |
| Adelphi | 2.3 |
| Baron | 3.7 |
| Bonnieblue | 2.7 |
| Brunswick | 1.7 |
| Fylking | 5.0 |
| Glade | 2.0 |
| Kenblue | 4.3 |
| Majestic | 3.0 |
| Merion | 2.3 |
| Nugget | 2.3 |
| Park | 7.3 |
| Pennstar | 4.7 |
| Sodco | 3.0 |
| Sydsport | 2.3 |
| Vantage | 4.7 |
| Victa | 4.0 |
| Windsor | 4.7 |
| LSD at 5% Level | 1.13 |

[a]1976 Kentucky Bluegrass Evaluations at FFR Cooperative.
P. R. Troutman

TABLE 22

| Variety | Growing Season Color[a] 4-24-70 | 5-21-71 | 6-10-70 | 9-9-72 | Color Mean |
|---|---|---|---|---|---|
| Rating: 1 = dark green; 9 = light green | | | | | |
| Plush | 3.0 | 4.0 | 4.0 | 4.3 | 3.8 |
| Cougar | 3.0 | 7.0 | 4.3 | 3.7 | 4.5 |
| Delta | 4.7 | 9.0 | 4.3 | 4.7 | 5.7 |
| Fylking | 3.1 | 5.0 | 5.0 | 4.4 | 4.4 |
| Geary | 5.3 | 8.7 | 7.3 | 5.3 | 6.6 |
| Kenblue | 5.0 | 8.7 | 7.0 | 4.7 | 6.4 |
| Merion | 2.7 | 3.0 | 4.3 | 2.0 | 3.0 |
| Newport | 3.8 | 7.3 | 4.4 | 4.7 | 5.0 |
| Nudwarf | 6.3 | 9.0 | 6.7 | 5.0 | 6.8 |

TABLE 22-continued

| Variety | Growing Season Color[a] | | | | Color |
|---|---|---|---|---|---|
| Nugget | 3.3 | 1.7 | 2.4 | 2.6 | 2.5 |
| Park | 4.7 | 9.0 | 8.3 | 5.3 | 6.8 |
| Sodco | 2.6 | 2.7 | 3.2 | 2.8 | 2.8 |
| S-21 | 8.0 | 8.3 | 8.3 | 7.7 | 8.1 |
| S. Dakota Common | 5.0 | 9.0 | 8.0 | 5.0 | 6.8 |
| Mean | | | | | 5.2 |
| LSD at 5% Level | 1.6 | 1.7 | 2.0 | 2.2 | |

[a]Kentucky Bluegrass Evaluations at FFR Cooperative.
P. R. Troutman

TABLE 23

| Variety | Early Spring Color at FFR Cooperative[a] Color |
|---|---|
| Rating: 1 = green; 9 = brown | |
| Plush | 4.2 |
| Cougar | 6.5 |
| Delta | 3.8 |
| Fylking | 5.6 |
| Geary | 3.2 |
| Kenblue | 4.3 |
| Merion | 4.7 |
| Newport | 6.0 |
| Nudwarf | 3.8 |
| Nugget | 8.2 |
| Park | 3.5 |
| Sodco | 5.2 |
| S-21 | 4.6 |
| S. Dakota Common | 4.8 |
| Mean | 4.9 |
| LSD at 5% Level | 2.4 |

[a]Kentucky Bluegrass Evaluations at FFR Cooperative.
P. R. Troutman

TABLE 24

| Variety | Late Fall-Early Winter Color at FFR Cooperative[a] Color[b] |
|---|---|
| Rating: 1 = green; 9 = brown | |
| Plush | 4.2 |
| Cougar | 7.1 |
| Delta | 7.9 |
| Fylking | 4.5 |
| Geary | 6.7 |
| Kenblue | 7.0 |
| Merion | 6.0 |
| Nudwarf | 5.8 |
| Nugget | 4.5 |
| Park | 6.5 |
| Sodco | 5.0 |
| S-21 | 7.2 |
| S. Dakota Common | 7.1 |
| Mean | 6.1 |
| LSD at 5% Level | 1.0 |

[a]Bluegrass Evaluations at FFR Cooperative.
P. R. Troutman

TABLE 25

| Variety | Leaf Blade Length (cm) | Leaf Blade Width (mm) | Leaf Blade Angle (degrees) |
|---|---|---|---|
| Plush | 20.4 | 3.2 | 36.0 |
| Fylking | 22.6 | 2.1 | 42.0 |
| Merion | 21.3 | 3.4 | 51.0 |
| Nugget | 17.6 | 2.2 | 50.0 |
| LSD at 5% Level | 3.40 | .62 | 8.56 |

[a]1974 Greenhouse Evaluation at FFR Cooperative, West Lafayette, Indiana. Plants grown from tillers and replicated 6 times.
P. R. Troutman

TABLE 26

| Variety | Thatch Depth at the University of Illinois[a] Centimeters |
|---|---|
| Plush | 1.3 |
| Adelphi | 1.2 |
| Baron | 1.4 |
| Bonnieblue | 1.0 |

TABLE 26-continued

| Variety | Thatch Depth at the University of Illinois[a] Centimeters |
|---|---|
| Brunswick | 1.5 |
| Fylking | 1.3 |
| Galaxy | 1.2 |
| Glade | 1.5 |
| Kenblue | 1.0 |
| Majestic | 1.4 |
| Merion | 1.0 |
| Monopoly | 1.1 |
| Nugget | 1.5 |
| Park | .7 |
| Pennstar | 1.2 |
| Sodco | 1.4 |
| Sydsport | 1.2 |
| Vantage | 1.0 |
| Victa | 1.5 |
| Windsor | 1.2 |

[a]1972 Regional Kentucky Bluegrass Trials at the University of Illinois.
A. J. Turgeon

TABLE 27

Root Strength at Virginia Polytechnic Institute and State University[a]

| Variety | 6 weeks growth | 8 weeks growth | Mean |
|---|---|---|---|
| Measured in pounds of force required to pull one square foot of sod from soil surface. | | | |
| Plush | 325 | 345 | 335 |
| Adelphi | 415 | 385 | 400 |
| Baron | 365 | 183 | 274 |
| Bonnieblue | 338 | 258 | 298 |
| Brunswick | 333 | 210 | 272 |
| Fylking | 373 | 185 | 279 |
| Galaxy | 310 | 245 | 278 |
| Glade | 345 | 178 | 262 |
| Kenblue | 252 | 353 | 302 |
| Majestic | 425 | 278 | 351 |
| Merion | 315 | 218 | 266 |
| Monopoly | 343 | 283 | 313 |
| Nugget | 423 | 225 | 325 |
| Park | 248 | 260 | 254 |
| Pennstar | 323 | 218 | 270 |
| Sodco | 328 | 280 | 304 |
| Sydsport | 410 | 268 | 339 |
| Vantage | 350 | 395 | 372 |
| Victor | 386 | 260 | 323 |
| Windsor | 308 | 335 | 322 |

[a]1972 Regional Kentucky Bluegrass Trials at Virginia Polytechnic Institute and State University.
R. E. Schmidt

TABLE 28

Heat Tolerance of Kentucky Bluegrass Cultivars at Virginia Polytechnic Institute and State University[a]

| Variety | % Green After Heat | Root Strength Pounds | % Ground Cover |
|---|---|---|---|
| Plush | 53 | 85 | 72 |
| Adelphi | 30 | 58 | 58 |
| Baron | 40 | 76 | 72 |
| Bonnieblue | 37 | 59 | 53 |
| Brunswick | 52 | 65 | 73 |
| Fylking | 33 | 41 | 42 |
| Galaxy | 8 | 56 | 50 |
| Glade | 35 | 43 | 50 |
| Kenblue | 65 | 98 | 77 |
| Majestic | 30 | 56 | 45 |
| Merion | 33 | 77 | 53 |
| Monopoly | 43 | 46 | 52 |
| Nugget | 38 | 62 | 47 |
| Park | 48 | 93 | 70 |
| Sodco | 45 | 76 | 68 |
| Sydsport | 35 | 61 | 57 |
| Vantage | 35 | 78 | 45 |
| Victa | 35 | 50 | 55 |
| Windsor | 40 | 70 | 73 |

[a]1972 Regional Kentucky Bluegrass Trials at Virginia Polytechnic Institute and State University.
R. E. Schmidt

TABLE 29

Lodging Resistance at Spokane, Washington[a]

| Variety | |
|---|---|
| Rating: 1 = Lodged; 5 = Erect | |
| Plush | 3.2 |
| Cougar | 4.8 |
| Fylking | 1.0 |
| Kenblue | 3.8 |
| Merion | 3.5 |
| Newport | 4.5 |
| Nugget | 5.0 |
| Sodco | 3.5 |
| S. Dakota Common | 3.0 |
| LSD at 5% Level | 1.98 |

[a]1969 FFR Kentucky Bluegrass Seed Production Evaluation at Spokane, Washington
Keith Wigen

TABLE 30

Seed Head Height at Spokane, Wash.[a]

| Variety | Height |
|---|---|
| Rating: 1 = short culm; 5 = tall culm | |
| Plush | 4.0 |
| Cougar | 3.0 |
| Fylking | 2.8 |
| Kenblue | 4.0 |
| Merion | 3.5 |
| Newport | 4.0 |
| Nugget | 1.0 |
| Sodco | 3.0 |
| S. Dakota Common | 4.5 |
| LSD at 5% Level | 1.30 |

[a]1969 FFR Kentucky Bluegrass Seed Production Evaluation at Spokane, Washington.
Keith Wigen

TABLE 31

Seed Head Emergence at Spokane, Washington[a]

| Variety | Avg. Rating[b] |
|---|---|
| Plush | 3.0 |
| Fylking | 3.0 |
| Kenblue | 3.5 |
| Merion | 1.5 |
| Newport | 3.5 |
| Sodco | 2.5 |
| S. Dakota Common | 3.5 |
| Nugget | 4.0 |

[a]1969 FFR Kentucky Bluegrass Seed Production Evaluation at Spokane, Washington.
Keith Wigen
[b]1 = no head emergence
2 = 1 - 25% emergence
3 = 50 - 75% emergence
4 = 75 - 100% emergence

TABLE 32

Seed Yield Evaluation at Spokane, Washington[a]

| Variety | 1970 Mean Seed Yield kg/ha | 1971 Mean Seed Yield kg/ha | 2-Year Mean kg/ha |
|---|---|---|---|
| Plush | 326.17 | 929.59 | 627.88 |
| Fylking | 244.63 | 1,223.15 | 733.89 |
| Kenblue | 212.06 | 962.34 | 587.20 |
| Merion | 195.66 | 848.05 | 521.86 |
| Newport | 130.51 | 782.81 | 1456.66 |
| Nugget | 81.54 | 521.88 | 301.71 |
| Sodco | 97.94 | 538.18 | 318.06 |
| S. Dakota Common | 163.09 | 913.12 | 538.11 |
| Mean | | | 510.67 |
| LSD at 5% Level | 130.51 | 375.10 | |

[a]1969 FFR Kentucky Bluegrass Seed Production Evaluation at Spokane, Washington.
Keith Wigen

TABLE 33

Seed Size and Color at FFR Cooperative[a]

| Variety | Seed Length (mm) | Seed Width (mm) | Seed Color |
|---|---|---|---|
| Rating: 1 = light tan, 9 = dark brown | | | |
| Plush | 2.9 | .69 | 6.3 |

TABLE 33-continued

| Variety | Seed Size and Color at FFR Cooperative[a] Seed Length (mm) | Seed Width (mm) | Seed Color |
|---|---|---|---|
| Adelphi | 2.6 | .61 | 8.0 |
| Baron | 2.5 | .58 | 3.0 |
| Bonnieblue | 2.7 | .69 | 5.7 |
| Fylking | 2.8 | .76 | 6.0 |
| Glade | 2.5 | .56 | 3.3 |
| Kenblue | 2.5 | .55 | 2.7 |
| Majestic | 2.5 | .66 | 6.2 |
| Merion | 2.4 | .61 | 1.0 |

TABLE 33-continued

| Variety | Seed Size and Color at FFR Cooperative[a] Seed Length (mm) | Seed Width (mm) | Seed Color |
|---|---|---|---|
| Nugget | 3.2 | .79 | 9.0 |
| LSD at 5% Level | .169 | .004 | 1.38 |

[a]Seed Characteristics Evaluation at FFR Cooperative.
P. R. Troutman

What is claimed is:

1. A new and distinct variety of bluegrass plant, *Poa pratensis,* substantially as described and illustrated, and particularly characterized by a medium-green color, highly apomictic, vigorous rhizome production, and good disease tolerance.

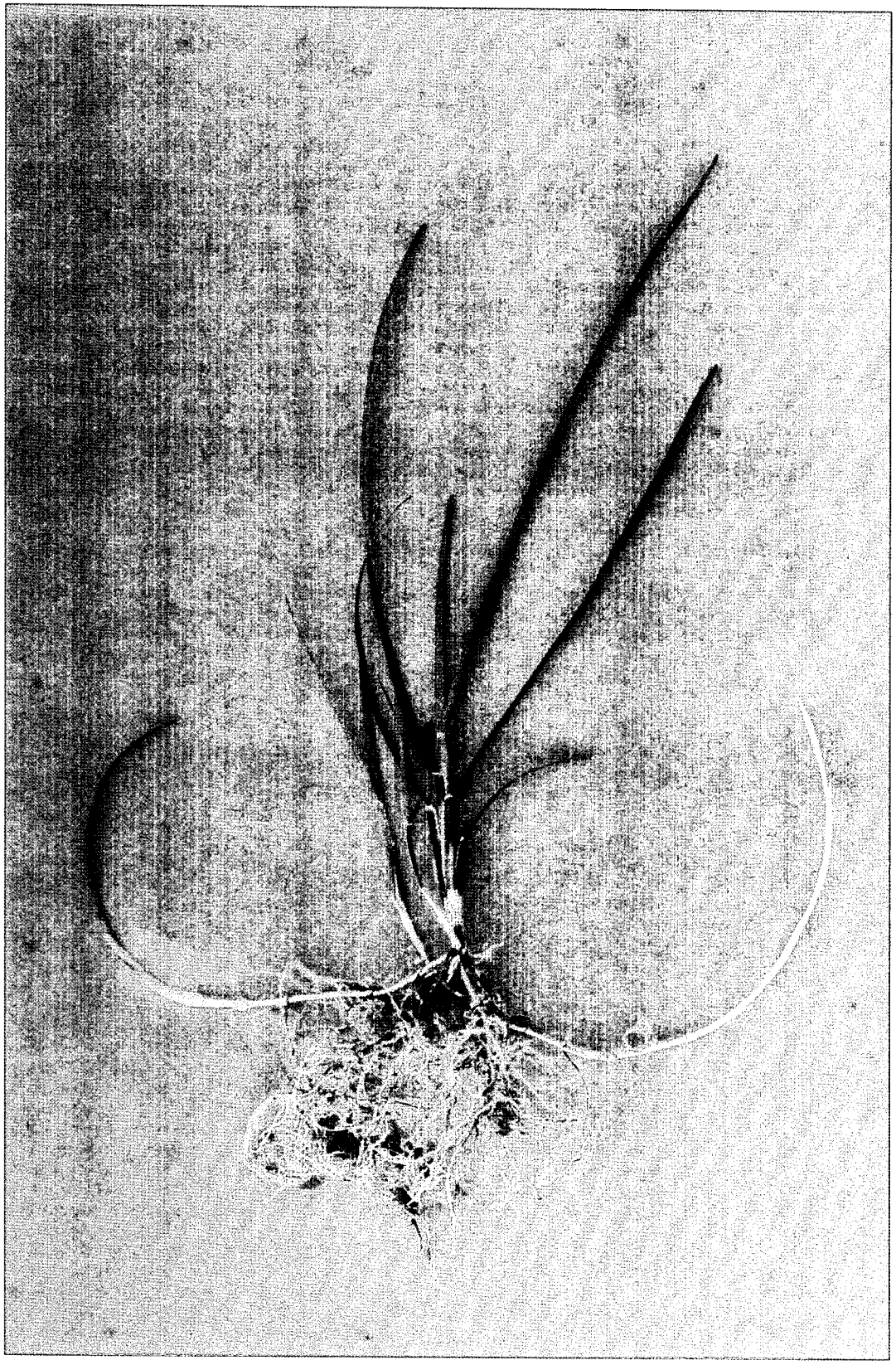

* * * * *